United States Patent [19]
Peterson

[11] Patent Number: 5,538,500
[45] Date of Patent: Jul. 23, 1996

[54] POSTOPERATIVE WOUND DRESSING

[76] Inventor: Donald A. Peterson, 15601 SW. April La., Portland, Oreg. 97224

[21] Appl. No.: 385,439

[22] Filed: Feb. 8, 1995

[51] Int. Cl.$^6$ ..................................... A61F 5/00
[52] U.S. Cl. ................. 602/48; 602/20; 602/26; 602/43; 602/54; 602/62
[58] Field of Search .................... 602/5, 26, 23, 602/41, 48, 51, 52, 54, 56

[56] References Cited

U.S. PATENT DOCUMENTS

| | | |
|---|---|---|
| 2,690,747 | 10/1954 | Frallic . |
| 3,113,568 | 12/1961 | Robins . |
| 3,194,234 | 7/1965 | Duckman et al. . |
| 3,245,406 | 4/1966 | Chardack . |
| 3,463,147 | 8/1969 | Stubbs ............................... 602/26 |
| 3,888,244 | 6/1975 | Lebold . |
| 4,176,664 | 12/1979 | Kalish . |
| 4,205,674 | 6/1980 | Porat et al. . |
| 4,269,181 | 5/1981 | Delannoy . |
| 4,630,603 | 12/1986 | Greenway . |
| 4,905,678 | 3/1990 | Cumin et al. . |
| 4,944,958 | 7/1990 | Langen et al. . |
| 4,977,893 | 12/1990 | Hunt . |
| 5,037,810 | 8/1991 | Saliba, Jr. . |
| 5,111,985 | 5/1992 | Lapeyre .............................. 225/51 |
| 5,267,952 | 12/1993 | Gardner . |
| 5,324,252 | 6/1994 | Libbey et al. ....................... 602/59 |
| 5,328,450 | 7/1994 | Smith et al. ........................ 602/59 |

*Primary Examiner*—Richard J. Apley
*Assistant Examiner*—Kim M. Lee
*Attorney, Agent, or Firm*—Kolisch, Hartwell, Dickinson, McCormack & Heuser

[57] ABSTRACT

A unitary medical dressing is provided which includes a generally elastic bandage wrap configured for rapid attachment to a wearer, a generally inelastic absorbent pad affixed to the bandage wrap, a medicated, non-adherent gauze mesh affixed to the absorbent pad opposite the bandage wrap, and an adhesive affixed to the perimeter of the gauze mesh so as to adhere to the wearer's skin.

20 Claims, 1 Drawing Sheet

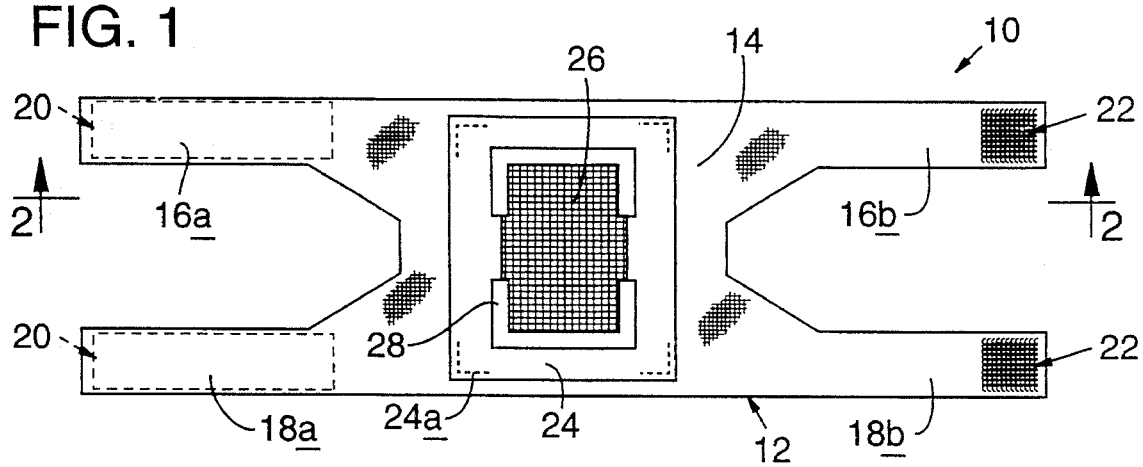
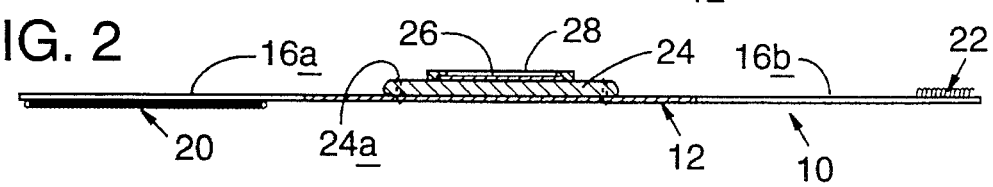
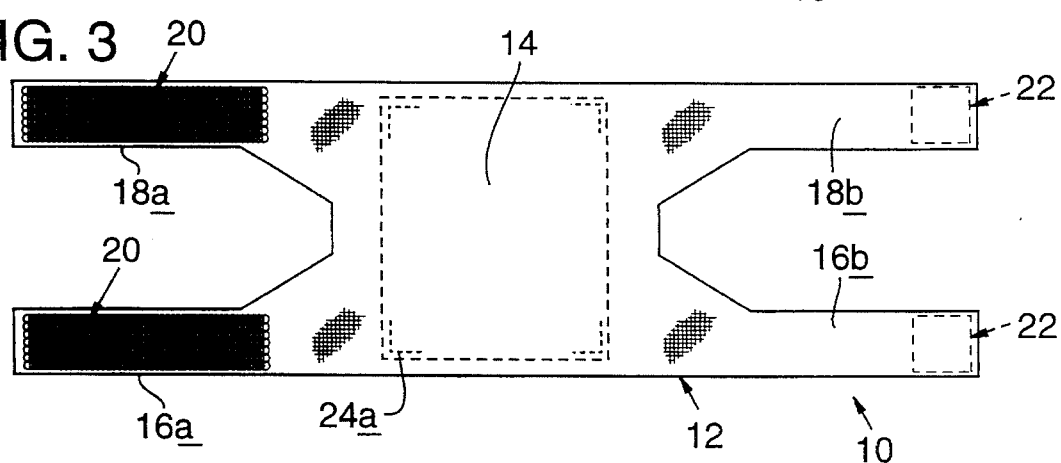
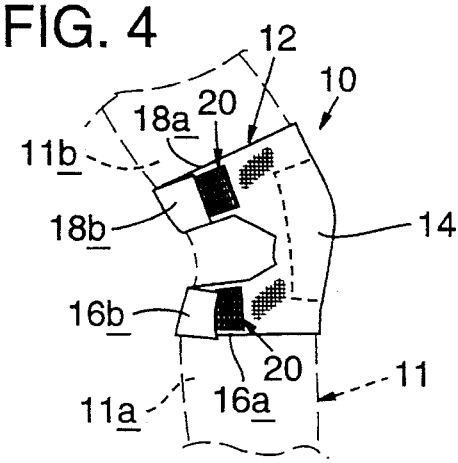
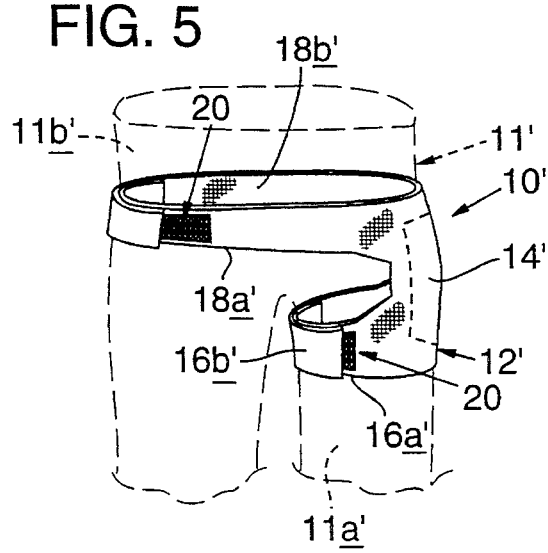

POSTOPERATIVE WOUND DRESSING

TECHNICAL FIELD

The present invention relates generally to medical dressings, and more particularly, to a ready-to-use postoperative wound dressing which adjusts to movements of the body while still protecting the wound. The invention is especially well-suited for use as a knee, elbow and/or hip dressing, and thus is described in that context below.

BACKGROUND ART

At present, the medical arts include a broad array of dressings, bandages and wound coverings, many of which consist of nothing more than a strip of fabric secured to a patient by some sort of fastening device. These dressings often are wrapped around the patient's body, the tightness of the wrap being relied upon to hold the dressing in place. Unfortunately, most conventional dressings tend to rotate or slide across the wound due to prying fingers or movement of the patient's body. This in turn may result in removal of any salves, ointments and/or medicaments from the dressing, leading to patient discomfort, and quite possibly to infection of the patient's wound. These undesirable effects may be exacerbated where the wound is uncovered, or where the dressing becomes loose, as is common where conventional dressings are used to cover a joint such as a knee, elbow or hip.

To address these problems, some physicians have proposed the use of adhesive tape to secure dressings in place over wounds, the tape generally being adhered directly to the patient's skin. Such an arrangement, however, is not entirely satisfactory. Adhesive tape, for example, may loosen due to body movement or patient perspiration, and may cause injury due to forces exerted on the patient's skin. Also, although adhesive tapes generally are capable of a degree of conformance to a body surface when first applied, they do not accommodate movement of the body surface itself. If applied over a joint, movement of the body may cause the tape to pull away from the skin, may damage the surrounding tissue, or may even restrict movement of the joint. Conventional use of adhesive tape, thus may lead to an increased potential for patient injury and/or infection of the wound.

Known dressings also have experienced problems due to wicking, an effect whereby bacteria or other contaminants may be drawn into a dressed wound along a fluid path. This problem has proven especially troublesome in postoperative dressings, particularly those which are asked to absorb substantial amounts of blood or other fluid from a wound. If unaddressed, such fluids can define a channel along which bacteria and other contaminants can pass to the wound. Again, infection or injury may result. Where the dressing is compressive, the potential for injury further may be increased due to the pressure which the dressing places on the anatomy surrounding the wound (e.g., blood vessels and nerves in the popliteal space). Such dressings also have been known to adhere to a wound or surrounding skin, raising the potential for shear injury to the skin when the dressing is removed. Additionally, known compressive dressings have been criticized as difficult to apply, particularly where the dressing is constructed at the time of application so as to produce a dressing for a patient-specific, or wound-specific use.

It is an object of the present invention to provide a dressing which may be readily secured to a wound and held in place during movements of the patient's body.

The invention also is intended to provide a compressive, protective barrier to infection and prying fingers without unduly restricting patient movement.

Another object of the invention is to provide a dressing with an absorbent pad configured to draw fluid away from a wound without providing increased access to bacteria or other contaminants.

It is yet another object of the invention to provide a medicated dressing which will not unduly adhere to the patient's wound or skin.

DISCLOSURE OF THE INVENTION

The present invention addresses the above-identified problems and concerns by provision of a unitary medical dressing which includes a generally elastic bandage wrap, a generally inelastic absorbent pad affixed to the bandage wrap, a medicated, non-adherent gauze mesh affixed to the absorbent pad opposite the bandage wrap, and an adhesive arranged at least partially about the perimeter of the gauze mesh so as to adhere to the wearer's skin.

The bandage wrap is defined with a wound-covering section from which extends a plurality of elongate strap sections, each strap section being configured to secure the dressing to the wearer by wrapping around a predetermined body part. The strap sections preferably are elastic, providing a somewhat compressive bandage wrap. As illustrated in the drawings, the dressing may be configured for use in covering a wound which is near a joint such as a knee, the strap sections being positioned to wrap around the patient's thigh and calf. Similarly, the dressing may be configured to cover a wound on the patient's hip, the strap sections correspondingly wrapping around the patient's waist and thigh. Each strap section is provided with a hook-and-loop fastener, allowing for quick application and removal of the dressing.

The absorbent pad is affixed to the interior of the wound-covering section of the bandage wrap, and the gauze mesh is affixed to the interior of the absorbent pad. The adhesive is arranged along at least portions of the gauze mesh perimeter, adhering to the patient's skin, and thereby fixing the position of the gauze mesh over the wound. The compressive effect of the bandage wrap, further secures the dressing to the patient so as to diminish the load on the adhesive. The absorbent pad draws fluid from the wound through the gauze mesh, but passage of bacteria or other contaminants to the wound is inhibited due to a bactericide or other medicament which is applied to the mesh. Further, the gauze mesh may be impregnated with a non-adherent compound such as petrolatum in order to avoid adhesion of the gauze to the wound.

These and other objects and advantages of the present invention will be more readily understood after a consideration of the drawings and the detailed description of the preferred embodiment which follows.

BRIEF DESCRIPTION OF THE DRAWINGS

FIG. 1 is an interior plan view of a medical dressing constructed in accordance with a preferred embodiment of the present invention.

FIG. 2 is sectional side view of the depicted medical dressing taken generally along line 2—2 of FIG. 1.

FIG. 3 is an exterior plan view of the medical dressing depicted in FIG. 1.

FIG. 4 is a side view of the medical dressing depicted in FIG. 1, the dressing having been applied so as to cover a wound on a patient's knee.

FIG. 5 is an isometric view of an alternative embodiment medical dressing, the dressing having been applied so as to cover a wound on a patient's hip.

DETAILED DESCRIPTION OF THE PREFERRED EMBODIMENT AND BEST MODE FOR CARRYING OUT THE INVENTION

Referring now to the drawings, and in particular FIGS. 1 through 4, there is shown a postoperative wound dressing 10 which includes a sheet-like bandage wrap 12 in the form of a resilient fabric strip. The bandage wrap preferably is formed of an elastic material which has some "stretch" or "give" along both its length and width so as to enhance the patient's comfort when the dressing is worn. The bandage wrap may, for example, be formed of neoprene, or of a similar elastic material such as that used in a conventional ACE™ bandage wrap.

As indicated, bandage wrap 12 includes a wound-covering section 14, and a plurality of elongate strap sections 16a, 16b, 18a, 18b. The wound-covering section overlies the patient's wound. The strap sections wrap around the patient's body to secure the dressing in place. The particular configuration of the strap sections and wound-covering section is dependant on the dressing's intended use.

In the embodiment depicted in FIGS. 1 through 4, dressing 10 is configured for use in dressing a knee wound. Bandage wrap 12 thus will be seen to include a wound-covering section which is intermediate the strap sections, each strap section extending outwardly from the wound-covering section to wrap the dressing around a portion of the patient's leg 11 (FIG. 4). The strap sections are arranged in substantially parallel fashion, and are paired so as to cooperatively wrap around the patient's leg. Strap sections 16a, 16b, for example, extend oppositely from the wound-covering section to wrap around the patient's calf 11a. Strap sections 18a, 18b are spaced from strap sections 16a, 16b and extend oppositely from the wound-covering section to wrap around the patient's thigh 11b. The wound-covering section covers the patient's knee. The popliteal portion of the leg is thus left uncovered, allowing for mobility of the patient's leg.

Each strap section is provided with a fastener 20, 22, such fasteners being configured to secure the straps together, and thus to hold the bandage wrap on the patient's leg. The fasteners preferably take the form hook-and-loop fasteners, providing for rapid attachment and removal of the bandage wrap. Strap sections 16a, 18a are each provided with a strip of loop fastener material on the exterior surface of the bandage wrap. Strap sections 16b, 18b are each provided with a strip of hook fastener material on the interior surface of the bandage wrap. Strap sections 16b, 18b thus may be wrapped around the patient's leg until the hook fastener strips overlap the loop fastener strips such that the strap sections may be secured in place. The fasteners are made adjustable, the hook and loop fastener strips having lengths which allow for varying degrees of overlap. By securing hook fastener strips 22 to different portions of loop fastener strips 20, it is possible to adjust the tightness of the wrap, and thus to control the compression on the wound.

Those skilled will appreciate that the fasteners alternatively may take the form of an adhesive or other chemical or mechanical fastening device, and may be adapted for either single or repeated use. Similarly, the bandage wrap may employ more or fewer strap sections than shown, and may strap sections which are configured to extend entirely around the wearer to fasten to the wound-covering section rather than to another strap section.

The dressing also includes an absorbent pad 24 which is affixed to the interior surface of the wound-covering section of bandage wrap 12. Pad 24 is affixed centrally to the wound-covering section, preferably via a reliable securement device such as stitching 24a. Instead of stitching, however, the absorbent pad may be attached to the bandage wrap by a permanent adhesive, or by a temporary adhesive which permits removal of a used pad and substitution of a new pad. Furthermore, the absorptive pad need not be secured to the bandage wrap entirely about its circumference, but rather may be secured on only two sides, or in the four corners as shown in FIGS. 1 and 3.

The absorbent pad may be woven, knitted, or otherwise constructed to provide for the absorption of fluid (e.g., blood or serous fluid) which drains from the patient's wound. In the preferred embodiment, the pad is woven from hydrophilic fibers such as hydrophilic cotton or fibrane, but other hydrophilic materials (including nonwoven hydrophilic materials such as bonded fibrous materials) could be used without departing from the invention as defined herein. The thickness of the pad is not critical to the invention, it being dependent upon the absorption characteristics of the material used. A typical useful thickness of an absorptive cotton pad, however, would be approximately 0.5-inches to 1.5-inches thick.

In accordance with one feature of the invented dressing, it will be appreciated that the absorptive pad may be formed of a generally inelastic material such as cotton or linen so as to limit stretch of the dressing in the area of the wound. This in turn will reduce the potential for injury which might otherwise result from external forces on the dressing. Also, because the bandage wrap is generally elastic, the strap sections will maintain the elastic nature of the dressing as a whole.

A gauze mesh 26 is affixed centrally to absorbent pad 24, such gauze mesh being secured centrally to the interior of the absorbent pad, preferably by some sort of stitching or adhesive as was previously described in connection with the absorbent pad. In the preferred embodiment, the gauze mesh is adapted to treat the patient's wound, being impregnated with a bactericide (e.g., providone-iodine or chloramine-T) or other medicament which avoids infection of the wound. The gauze mesh also is impregnated with a lubricant such as petrolatum, making for non-adherent contact between the dressing and the wound. Both the bactericide and the lubricant, it will be appreciated, are applied to the wound do to micro-movement of the gauze mesh.

In order to provide for proper wound drainage, the gauze mesh is of a density which will allow passage of fluids from the wound to the absorbent pad. Passage of bacteria to the wound, however, will be inhibited by the bactericide on the gauze mesh. The gauze mesh preferably is chosen so as to define a 25-mesh screen, allowing pad 24 to draw fluids through the openings in the gauze mesh. The gauze mesh thus generally will be less dense than a fine or regular gauze mesh. The gauze mesh may, however, be chosen in accordance with the particular drainage requirements of the to-be-treated wound.

As best indicated in FIG. 1, an adhesive such as tape 28 is applied to the gauze mesh along at least a portion of its perimeter, the tape being configured with an adhesive surface facing the patient's skin so as to fix the gauze mesh in place over the patient's wound. In the preferred embodiment, the adhesive tape is a double-sided foam tape which adheres on one side to the gauze mesh, and adheres on the other side to the patient's skin. The tape thus serves both to center the gauze mesh over the wound, and to improve protection of the wound by defining at least a partial barrier to contaminants, irritants or intrusive fingers which might otherwise disturb the wound.

It will be noted, however, that the tape need not extend entirely around the gauze mesh perimeter, the depicted dressing including noticeable gaps in the tape. These gaps are chosen to minimize stress on the patient's skin and to allow crenelation of the generally inelastic absorbent pad. In the-current embodiment, for example, these gaps correspond to that portion of the knee where the skin expands and contracts most upon bending of the knee.

The adhesive tape should be formed of an inert material and should be non-irritating to the skin. For comfort, the tape should be light weight, and should be sufficiently elastic so as not to restrict either circulation or surface dimension changes in that part of the skin which is covered by the tape. Synthetic sponge materials of the type including a foamed mass of plastic are eminently suitable for such use. They are resiliently yieldable, and readily conformable to the body surface, while at the same time possessing great tensile strength.

In order to preserve the sterile nature of the dressing, the adhesive tape further may be used to hold a sterile covering over the gauze mesh prior to use of the dressing. The covering is removed at the time of use to expose the gauze mesh, and the dressing is applied such that the gauze mesh covers the wound in the manner described above.

The dressing thus defines a non-adherent, bacteriocidal barrier with absorption characteristics which provide adequate drainage from a wound. The gauze mesh is held in place over the wound by a resilient adhesive tape, the tape generally being configured to provide a protective barrier about at least a portion of the wound without unduly limiting the patient's ability to flex. The bandage wrap provides compression to the wound, but works together with the adhesive tape to hold the dressing in place.

FIG. 5 shows a wound dressing 10' formed in accordance with an alternative embodiment of the present invention so as to provide for use of the dressing to cover a wound on a patient's hip 11'. Dressing 10' is similar to dressing 10, the principle difference being in the character of the bandage wrap 12'. As indicated, bandage wrap 12' is configured to place its wound-covering section 14' over the patient's hip when the dressing is applied. Bandage wrap 14' thus is specially provided with strap sections 16a', 16b', 18a', 18b' which wrap around the patient's waist and thigh. Strap sections 16a', 16b' cooperate to wrap around the patient's thigh 11a'. Strap sections 18a', 18b' cooperate to wrap around the patient's waist 11b'.

While the present invention has been shown and described with reference to the foregoing operational principles and preferred embodiment, it will be apparent that to those skilled in the art that various changes in form and detail may be made without departing from the spirit and scope of the invention as defined by the appended claims.

I claim:

1. A unitary medical dressing comprising:
   a bandage wrap including a wound-covering section from which extends at least one elongate strap section, said strap section being configured to secure the bandage wrap to a wearer;
   an absorbent pad affixed to said wound-coveting section for placement over a wound upon securing said bandage wrap to the wearer;
   a gauze mesh affixed to said absorbent pad opposite said bandage wrap so as to cover the wound upon securing said bandage wrap to the wearer; and
   an adhesive arranged substantially about a perimeter of said gauze mesh and overlying said gauze mesh to frame said gauze mesh, said adhesive being a sole source of adhesion to the wearer and thereby, fixing said gauze mesh to a wearer in place over the wound upon securing said bandage wrap to the wearer.

2. The dressing of claim 1, wherein said bandage wrap is formed of a generally elastic material.

3. The dressing of claim 2, wherein said absorbent pad is formed of a generally inelastic material.

4. The dressing of claim 1, wherein said gauze mesh is medicated.

5. The dressing of claim 1, wherein said gauze mesh is impregnated with a bactericide.

6. The dressing of claim 5, wherein said gauze mesh is further impregnated with a petrolatum blend.

7. The dressing of claim 1, wherein said gauze mesh is of a density which allows passage of fluids from the wound to said absorbent pad.

8. The dressing of claim 1, wherein said gauze mesh is approximately a 25-mesh screen.

9. The dressing of claim 1, wherein said adhesive is an adhesive tape secured to said gauze mesh perimeter.

10. The dressing of claim 1, wherein said adhesive is a foam tape.

11. The dressing of claim 1, wherein said adhesive is a double-sided tape which adheres on one side to said gauze mesh, and on another side to the wearer's skin.

12. A unitary medical dressing comprising:
   a generally elastic non-adherent bandage wrap including a wound-covering section from which extends a plurality of elongate strap sections, each strap section being configured to secure the bandage wrap to a wearer by wrapping about a predetermined portion of the wearer's body;
   a generally inelastic absorbent pad affixed to said wound-covering section for placement over a wound upon securing said bandage wrap to the wearer;
   a medicated, non-adherent gauze mesh affixed to said absorbent pad opposite said bandage wrap so as to cover the wound, said gauze mesh being configured to allow passage therethrough of fluids from the wound to said absorbent pad; and
   an adhesive tape secured to said gauze mesh substantially about a perimeter of said gauze mesh and overlying said gauze mesh to frame said gauze mesh, said adhesive tape being a sole source of adhesion to the wearer and including an adhesive surface which faces opposite said gauze mesh to adhere to the wearer's skin in an area surrounding, but not overlying the wound to fix said gauze mesh in place over the wound.

13. The dressing of claim 12, wherein said strap sections extend from said wound-covering section in parallel fashion.

14. The dressing of claim 12, wherein said bandage wrap includes at least two spaced-apart strap sections which extend in parallel fashion from said wound-covering section to provide a first strap section configured to wrap around a predetermined first portion of the wearer's body, and a second strap section configured to wrap around a predetermined second portion of a wearer's body.

16. The dressing of claim 14, wherein said first strap section is configured to wrap around the wearer's calf and said second strap section is configured to wrap around the wearer's thigh.

16. The dressing of claim 14, wherein said first strap section is configured to wrap around the wearer's thigh and said second strap section is configured to wrap around the wearer's waist.

17. The dressing of claim 12, wherein each strap section includes an adjustable fastener, each fastener being adjustable to vary tightness of said bandage wrap.

18. The dressing of claim 17, wherein said fastener are a hook-and-loop fasteners.

19. The dressing of claim 12, wherein each strap section is paired with another strap section, each strap section pair being configured to wrap oppositely around the wearer's body and fasten to one another to hold said bandage wrap in place.

20. A unitary medical dressing configured for removable securement to a wearer to cover and protect a wound, said dressing comprising:

a bandage wrap including a wound-covering section, and a plurality of elongate, generally elastic strap sections which extend in parallel fashion from said wound-covering section to wrap about predetermined portions of the wearer's body, each strap section being paired with another strap section and configured to wrap oppositely around the wearer's body an fasten to another strap via an adjustable fastener to provide for adjustment of compression on the wound;

a generally inelastic absorbent pad affixed to said wound-coveting section for placement over the wound upon applying said bandage wrap to the wearer;

a medicated, non-adherent gauze mesh affixed to said absorbent pad opposite said bandage wrap so as to cover the wound, said gauze mesh being configured to allow passage therethrough of fluids from the wound to said absorbent pad, but to inhibit passage of bacteria toward the wound; and a pair of facing, generally C-shaped adhesive tape strips secured to said gauze mesh substantially about a perimeter of said gauze mesh and overlying said absorbent pad, said adhesion tape strips being a sole source of adhesion to the wearer, said adhesive tape strips each including an adhesive surface which faces opposite said gauze mesh to adhere to the wearer's skin in an area surrounding, but not overlying, the wound, thus fixing said gauze mesh both laterally and translationally in place over the wound while allowing crenelation of the generally inelastic absorbent pad.

* * * * *